(12) United States Patent
Crooks et al.

(10) Patent No.: US 6,638,994 B2
(45) Date of Patent: Oct. 28, 2003

(54) AQUEOUS SUSPENSION OF NANOPARTICLES COMPRISING AN AGROCHEMICAL ACTIVE INGREDIENT

(76) Inventors: Regan Crooks, 32 Powell Ct., Hightstown, NJ (US) 08520; Mathieu Joanicot, 505 Bergen St., Lawrenceville, NJ (US) 08648; Robert K. Prud'Homme, 31 West Long Dr., Lawrenceville, NJ (US) 08648; Joel Coret, 9, Sundew Way, Robbinsville, NJ (US) 08691

( * ) Notice: Subject to any disclaimer, the term of this patent is extended or adjusted under 35 U.S.C. 154(b) by 0 days.

(21) Appl. No.: 10/112,131

(22) Filed: Mar. 29, 2002

(65) Prior Publication Data

US 2003/0013799 A1 Jan. 16, 2003

Related U.S. Application Data

(60) Provisional application No. 60/280,433, filed on Mar. 30, 2001.

(51) Int. Cl.[7] .................................................. A01N 25/30
(52) U.S. Cl. ..................... 523/122; 504/116.1; 504/156; 504/172; 504/360; 504/361; 504/362
(58) Field of Search ............... 504/116.1, 118, 504/121, 123, 156, 172, 560, 360, 361, 362, 365, 366; 514/951; 523/122

(56) References Cited

U.S. PATENT DOCUMENTS

| | | | |
|---|---|---|---|
| 4,282,209 A | 8/1981 | Tocker | 424/81 |
| 4,435,383 A | 3/1984 | Wysong | 424/78 |
| 4,722,838 A | 2/1988 | Tocker | 424/81 |
| 5,118,528 A | 6/1992 | Fessi | 427/213.36 |
| 5,510,118 A | 4/1996 | Bosch | 424/489 |
| 5,683,723 A | 11/1997 | Spenleuhauer | 424/501 |
| 5,766,635 A | 6/1998 | Spenleuhauer | 424/489 |
| 6,074,441 A | 6/2000 | Schulte | 23/300 |
| 2002/0098221 A1 * | 7/2002 | Taranta et al. | 424/405 |

FOREIGN PATENT DOCUMENTS

| | | | |
|---|---|---|---|
| EP | 0083437 | 7/1983 | .......... A01N/25/04 |
| EP | 0103171 | 3/1984 | .......... A01N/25/04 |
| EP | 0253682 | 1/1988 | .......... A01N/25/04 |
| EP | 0589838 | 3/1994 | .......... A01N/25/04 |
| EP | 1023832 | 8/2000 | .......... A01N/25/04 |
| WO | WO 97/13503 | 4/1997 | ............ A61K/9/16 |
| WO | WO 99/18787 | 4/1999 | .......... A01N/25/30 |
| WO | WO 99/65301 | 12/1999 | .......... A01N/25/04 |
| WO | WO 00/60942 | 10/2000 | .......... A01N/25/30 |
| WO | WO 01/93679 | 12/2001 | .......... A01N/25/30 |

OTHER PUBLICATIONS

J. Microencapsulation, 2000, vol. 17, No. 2, 195–205, "Polyϵ–caprolactone nanoparticles. . . ", A.L. Le Roy Boehm, R. Zerrouk, and H. Fessi.

* cited by examiner

*Primary Examiner*—Edward J. Cain
*Assistant Examiner*—Katarzyna W. Lee

(57) ABSTRACT

The invention relates to an aqueous suspension of particles, said particles comprising an organic active ingredient. A controlled release of the ingredient occurs. The invention is especially suitable for the controlled release of organic agrochemical active ingredients useful in crop sciences, such as pesticides.

24 Claims, No Drawings

AQUEOUS SUSPENSION OF NANOPARTICLES COMPRISING AN AGROCHEMICAL ACTIVE INGREDIENT

This application claims priority under 35 U.S.C. §§119 and/or 365 to No. 60/280,433 filed in the United States on Mar. 30, 2001, the entire content of which is hereby incorporated by reference.

BACKGROUND OF THE INVENTION

The invention relates to an aqueous suspension of particles, said particles comprising an organic active ingredient. A controlled release of the ingredient occurs. The invention is especially suitable for the controlled release of organic agrochemical active ingredients useful in crop sciences, such as pesticides.

Controlled release of an active organic ingredient is of interest in many fields. Depending on the ingredient to be released and its use, different issues may be addressed. Some uses require the ingredient to be released slowly at low concentration. Some uses require the ingredient to be released slowly, or quickly, at high concentrations.

Using a liquid carrier for releasing an active ingredient is of great interest in many fields. The ingredient to be released may be easily spread onto a surface, for example by spraying, injected into a body to be treated, or added into a formulation. For example, spreading emulsions of an organic ingredient in water is known. Spreading or injecting a suspension of particles comprising an active ingredient is also known. The size of an emulsion or of particles may be of great importance to control the exchange of an active ingredient with the object it is supposed to interact with. Usually, the higher the surface area to volume is, the more efficient the carrier is. Controlling the size may also avoid a spreading device such as a nozzle to clog on spraying.

Therefore, both controlling the size of a carrier of an active ingredient and controlling the concentration of the active ingredient may be of great importance, for technical, environmental, or economical reasons.

Especially in crop sciences, slow release of pesticide systems offer several advantages. Firstly, controlled release systems are more economical, as fewer applications to the crop are needed. Secondly, these systems offer safety to the environment by preventing pesticide overuse and subsequent runoff or soil leaching into waterways. Thirdly, they also reduce phytotoxicity to crops where large doses of conventional formulations can be phytotoxic. Controlled release systems also reduce the risk of toxicity to the people applying the pesticide in the fields.

Traditionally, one-phase controlled release pesticidal compositions are prepared, and involve co-melting a pesticide with a suitable polymer, followed by grinding to a desired size. This method suffers many disadvantages, including the requirement of the pesticide to be milled and combined with wetting and dispersing agents to produce a suspension concentrate. Often these formulations are not homogenous and the particle sizes are large, in the order of 10 μm.

Another technique to produce pesticidal particles is microencapsulation. One method of microencapsulation is via interfacial polymerization. U.K patent GB 2,027,346 describes the encapsulation of insecticides (methomyl and oxamyl) via microencapsulation. Particles of 30–130 μm are obtained.

Another form of microencapsulation utilizes phase separation where an organic solution of polymer is an encapsulating medium (for encapsulating a hydrophobic active material). Upon addition to a non-solvent the active material is encapsulated by the polymer. U.S. Pat. Nos. 4,282,209 and 4,722,838 describe such a precipitation of an insecticide (methomyl and oxamyl) embedded in a preformed polymer. The latter patent is an improvement on the former, requiring only mild agitation of the organic solvent and water during precipitation. However, 2 parts of the polymer (poly(methyl methacrylate)) to one part of the active are required to form particles of 50 μm in diameter, and a surfactant is also needed to disperse the particles in the aqueous phase.

U.S. Pat. No. 4,435,383 describes a dispersion of particles obtained by dispersing in water a solid composition comprising a cross-linked polymer and an active ingredient. The size of the particles is greater than 5 μm.

Nanoparticles of polymers are known. U.S. Pat. No. 5,145,684 describes nanoparticulate compositions consisting of a poorly soluble therapeutic or diagnostic agent with a non-crosslinked surface stabilizer adsorbed on the surface. It is recognized that not all surface stabilizers will produce a stable, non-agglomerated nanoparticulate composition for all agents. Thus, there is a need to identify new surface stabilizers that have superior properties over the known surface stabilizers.

Boehm et al., J. Microencapsulation, 17, 195 (2000) teach pesticidal active ingredients have been formulated by nanoprecipitation with a poly(ε-caprolactone) polymer and a surfactant. Nanoparticles of 200–300 nm were formed using at least 1:1 surfactant to active ingredient. Liu et al., Journal of Applied Polymer Science, 79, 458 (2001) describe incorporating the fungicides tebuconazole and chlorothalonil into nanoparticles of 100–250 nm in diameter, using a copolymer polyvinylpyridine-co-styrene and polyvinylpyridine (PVPy). It was found that the delivery of the biocides to wood via a polymer matrix showed improved efficacy compared to being introduced via a solution or liquid-liquid emulsion. However, a high ratio of polymer to active is required (at least 1:1) and surfactants such as Tween 80 are also necessary for stabilization of the nanoparticles.

U.S. Pat. No. 5,766,635 describes nanoparticles comprising a pharmaceutical active ingredient, and a polylactic copolymer. However, the ratio between the active ingredient and the copolymer is low (20% by weight). Such a low amount is not suitable in agrochemical formulations.

U.S. Pat. No. 5,510,118 describes a process for preparing therapeutic compositions containing nanoparticles. The process comprises using various surface modifiers and carrying out an expensive microfluidizing step. Obtained nanoparticles have a size of less than 400 nm, and consist of a solid therapeutic compound having the surface modifier absorbed on their surface.

U.S. Pat. No. 6,074,441 describes a process for producing ultrafine organic crystallization products, for example naphthalene, comprising an expensive atomizing step. The process comprises the use of a high amount of a surfactant (5 g for 0.75 g of a naphthalene chloroform solution).

U.S. Pat. No. 5,118,528 describes a process for making nanoparticles comprising the steps of combining (1) a first liquid phase comprising a film-forming compound, a biologically active substance and a surfactant, in a solvent, and (2) a non-solvent of the film-forming compound, to form a nanoparticles precipitate. The film-forming compound is a polymer such as polylactic acid, cellulose derivatives, or Arabic gum. The active substance is a pharmaceutical substance, or a fatty substance. Obtained nanoparticles comprise the film-forming compound, the active substance, and the surfactant. However, the ratio between the surfactant together with the film forming compound and the active substance is very high.

U.S. Pat. No. 5,683,723 describes a process for making polymeric nanoparticles by mixing a solution of a polymer and a non-solvent of said polymer. A surfactant is also used. The polymer is a polyoxyethylene-polylactic block copolymer. Said copolymer has a therapeutic effect, and no further organic ingredient is added.

Published International application WO 97/13503 describes the synthesis of drug nanoparticles by spray drying. According to this process a dispersion of nanoparticles of a drug in a polymeric matrix is obtained, and not an aqueous suspension of nanoparticles.

Published International application WO 97/18787 describes powder formulations comprising a water insoluble active and a copolymer dispersant, comprising α-β-unsaturated oxyacids, and further dispersion in an aqueous medium. The powder is obtained with powder-formation means, and comprises large particles.

Published International applications WO 00/60942 and WO 01/93679 describe powder formulations comprising an agrochemical and a styrene(meth)acrylic copolymer. The particle size of the powder is of 5 to 50 µm.

BRIEF SUMMARY OF THE INVENTION

The invention provides an aqueous suspension of nanoparticles comprising an organic water-insoluble agrochemical active ingredient. Both the small size of the particles, and the high concentration of active ingredient in the particle, are interesting for designing a controlled release of the agrochemical active ingredient.

Thus, the present invention is an aqueous suspension of nanoparticles, said nanoparticles comprising:

an amphiphilic compound comprising at least one hydrophilic moiety and at least one hydrophobic moiety, and
at least 50 parts by weight of an organic water-insoluble agrochemical active ingredient for 100 parts of the amphiphilic compound.

By "nanoparticles" is meant particles having a size of lower than or equal to 1060 nm. The particles size is defined as the size measured with a Malvern Mastersizer S version 2.18 device, and a size analysis performed assuming a polydisperse model and the Standard-Wet (3OHD) presentation that assumes that the particle is suspended in water. The size is the mass median diameter at which 50% of the sample is smaller and 50% is larger than this size.

Hence, the aqueous suspension may comprise particles with a size greater than 1060 nm, further to nanoparticles. But more preferably the more than 75% of the nanoparticles have a diameter of lower than 1060 nm.

Without being bound to any theory, it is believed that the nanoparticles in the suspension according to the invention comprise a solid core of the organic water-insoluble agrochemical active ingredient, and the amphiphilic compound around said core, the hydrophobic moiety interacting with the surface of the core, and the hydrophilic moiety interacting with water, or being at least partially dissolved in water.

The size of the nanoparticles according to the invention is preferably of lower than 600 nm. It is also usually of greater than 100 nm.

Nanoparticles comprised in the suspension according to the invention comprise an amphiphilic compound and at least an organic water-insoluble agrochemical active ingredient. The organic water-insoluble agrochemical active ingredient is not a polymeric compound. Hence, particles in suspensions according to the invention do not consist only of a polymeric compound with, optionally, a surfactant. Preferred water-insoluble organic agrochemical active ingredients are pesticides such as atrazine, cymoxanil or chlorothalanil, but the invention is also useful with other ingredients. The aqueous suspension of nanoparticles may also comprise an organic solvent. Such an organic solvent is usually used prior to the formation of the nanoparticles to dissolve, the organic water-insoluble agrochemical active ingredient. It is preferably a water-miscible solvent. It may be removed after the nanoparticles have been formed.

The nanoparticles comprise at least 50 parts by weight of the organic agrochemical active ingredient for 100 parts by weight of the amphiphilic compound. This amount is more preferably at least of 100, 200, and even of at least 500 parts, for 100 parts by weight of the amphiphilic compound.

The amphiphilic compound comprises at least one hydrophilic moiety and at least one hydrophobic moiety. The hydrophilic moiety is preferably a hydrophilic polymeric block. Di-block copolymers, that is block copolymers comprising one hydrophilic block, one hydrophobic block and, optionally, chain transfer units or specific end-chain units at the ends of blocks, are preferred.

An advantage of the invention is that there is a high surface area to volume of active ingredient. Applying the suspension onto a surface or introducing it into a medium avoids using more active ingredients than necessary to obtain the desired release and effect. Another advantage is that the amount of carrier (the amphiphilic compound in the instant invention) is low. It avoids using a large amount of a compound, such as a surfactant, that is not directly necessary for the purpose the active ingredient is used for. Hence, the suspensions according to the invention are cost effective and environment friendly.

DETAILED DESCRIPTION OF THE INVENTION

By agrochemical active compound it is meant a compound having an effect on a plant growth, whether by killing undesired organisms or avoiding development thereof, or by directly having an effect on the plant. Examples of organic water-insoluble agrochemical active ingredient include:

insecticides, for example selected from the group consisting of carbamates, such as methomyl, carbaryl, carbofuran, or aldicarb; organo thiophosphates such as EPN, isofenphos, isoxathion, chlorpyrifos, or chlormephos; organo phosphates such as terbufos, monocrotophos, or terachlorvinphos; perchlorinated organics such as methoxychlor; synthetic pyrethroids such as fenvalerate nematicide carbamates, such as oxamyl herbicides, for example selected from the group consisting of triazines such as metribuzin, hexaxinone, or atrazine; sulfonylureas such as 2-chloro-N-[(4-methoxy-6-methyl-1,3,5-triazin-2-yl)aminocarbonyl]-benzenesulfonamide; uracils (pyrimidines) such as lenacil, bromacil, or terbacil; ureas such as linuron, diuron, siduron, or neburon; acetanilides such as alachlor, or metolachlor; thiocarbamates such as benthiocarb (SATURN), triallate; oxadiazol-ones such as oxadiazon; phenoxyacetic acids such as 2,4-D; diphenyl ethers such as fluazifop-butyl, acifluorfen, bifenox, or oxyfluorfen; dinitro anilines such as trifluralin; glycine phosphonates such as glyphosate salts and esters; dihalobenzonitriles such as bromoxynil, or ioxynil fungicides, for example selected from the group consisting of nitrilo oximes such as cymoxanil (curzate); imidazoles such as benomyl, carbendazim, or thiophanate-methyl; triazoles such as triadimefon; sulfenamides such as captan; dithiocarbamates such as maneb, mancozeb, or thiram; chloronated aromatics such as chloroneb; dichloro anilines such as iprodione aphicides, for example selected in the group consisting of carbamates, such as pirimicarb, miticides, for example selected in the group consisting of propynyl sulfites such as propargite; triazapentadienes such as amitraz; chlorinated aromatics such as chlorobenzilate, or tetradifan; dinitrophenols such as binapacryl.

The organic water-insoluble agrochemical active ingredients may be comprised in the particles as a mixture of several ingredients. Especially preferred organic water-insoluble agrochemical active ingredients are atrazine, cymoxanil, chlorothalanil, cyproconazole, and tebuconazole.

The amphiphilic compound comprises at least one hydrophilic moiety and at least one hydrophobic moiety. The hydrophilic moiety is preferably a hydrophilic polymeric block. Hydrophilic blocks are homopolymer blocks or copolymer blocks comprising hydrophilic units (deriving from hydrophilic monomers or from units that are reacted to bercome hydrophilic). Hydrophilic blocks optionally comprise some hydrophobic units, but most of the units are hydrophilic. The hydrophobic moiety may be a polymeric or a non-polymeric moiety. The weight-average molecular weight of the hydrophilic block is preferably of greater than 1000 g/mol.

Examples of non polymeric hydrophobic moieties include alpha-{2,4,6-tris[1-(phenyl)ethyl]phenyl}-omega-hydroxy group. Such a moiety is particularly preferred in combination with organic active ingredient comprising at least an aromatic ring, such as atrazine. Preferred amphiphilic compounds comprising alpha-{2,4,6-tris[1-(phenyl)ethyl]phenyl}-omega-hydroxy group hydrophobic moiety comprise, as a hydrophilic polymeric block, poly(oxyethelene), poly(oxypropylene), or a poly(oxyethelene)-poly(oxypropylene) copolymer. An especially preferred amphiphilic compound is alpha-{2,4,6-tris[1-(phenyl)ethyl]phenyl}-omega-hydroxy poly(oxyethelene)-poly(oxypropylene) copolymer comprising from 2 to 8 moles of poly(oxypropylene) units and 16–30 units of poly(oxyeythylene) units. Such an amphiphilic compound is for example Soprophor 796/P, marketed by Rhodia.

Amphiphilic compounds comprising a polymeric hydrophobic moiety and a polymeric hydrophilic moiety are block copolymers. Di-block copolymers are preferred. Hydrophilic polymeric blocks are homopolymer blocks or copolymer blocks comprising hydrophilic units (deriving from hydrophilic monomers or from units that are reacted to become hydrophilic). Hydrophobic polymeric blocks are homopolymer blocks or copolymer blocks comprising hydrophobic units (obtained with hydrophobic monomers). Hydrophobic blocks optionally comprise some hydrophilic units, but most of the units are hydrophobic.

Examples of hydrophilic blocks include blocks comprising units deriving from monomers being:

unsaturated ethylenic monocarboxylic acids, unsaturated ethylenic dicarboxylic acids, monoalkyl esters of unsaturated ethylenic dicarboxylic acids or N-substituted derivatives of monoalkyl esters of unsaturated ethylenic dicarboxylic, amides of unsaturated carboxylic acids, ethylenic monomers comprising a sulphonic acid group, their alkali metal, their ammonium salts, ethylene oxide, or propylene oxide.

Examples of preferred hydrophilic blocks include blocks comprising units deriving from monomers being: acrylic acid (AA), methacrylic acid, itaconic acid, maleic acid, fumaric acid, 2-hydroxyethyl acrylate, 2-hydroxyethyl acrylate methacrylate, acrylamide (AM), methacrylamide, vinylsulphonic acid, vinylbenzenesulphonic acid, alpha-acrylamidomethylpropanesulphonic acid, 2-sulphoethyl methacrylate, 2-acrylamido-2-methylpropanesulphonic acid (AMPS), or styrenesulphonate (SS).

Examples of hydrophobic blocks include blocks comprising units deriving from monomers being:

esters of acrylic acid and of methacrylic acid with hydrogenated or fluorinated $C_1$–$C_{12}$ alcohols, vinyl nitrites having from 3 to 12 carbon atoms, carboxylic acid vinyl esters, vinyl halides, vinylamine amides, unsaturated ethylenic monomers comprising a secondary, tertiary or quaternary amino group, or unsaturated ethylenic monomers comprising a heterocyclic group comprising nitrogen, or Styrene.

Examples of preferred hydrophobic blocks include blocks comprising units deriving from monomers being: methyl acrylate, ethyl acrylate, propyl acrylate, n-butyl acrylate, isobutyl acrylate, 2-ethylhexyl acrylate, t-butyl acrylate, methyl methacrylate, ethyl methacrylate, n-butyl methacrylate, isobutyl methacrylate, acrylonitrile, methacrylonitrile, vinyl acetate, vinyl versatate, vinyl propionate vinylformamide, vinylacetamide, vinylpyridines, vinylimidazole, aminoalkyl (meth)acrylates, aminoalkyl (meth)acrylamides, dimethylaminoethyl acrylate, dimethylaminoethyl methacrylate, di-tert-butylaminoethyl acrylate, di-tert-butylaminoethyl methacrylate, dimethylaminomethylacrylamide or dimethylaminomethylacrylamide methacrylamide.

In a particular embodiment, the block copolymer has a weight-average molecular weight comprised between 1000 and 50000 g/mol, with a glass transition temperature of the hydrophilic block(s) being lower than 30° C. Polymers according to this particular embodiment have particularly good and suitable surfactant properties, to obtain nanoparticles.

Preferred block copolymers are di-block copolymers, that is block copolymers comprising one hydrophilic block, one hydrophobic block and, optionally chain transfer units or specific chain-end units at the ends of blocks. The presence of chain transfer units or specific end-chain units is usually a consequence of the process used for making the di-block copolymer.

Especially preferred di-block copolymers comprise two blocks comprising units deriving from mono-α-ethylenically unsaturated monomers.

Examples of processes for making di-block, or poly-blocks, copolymers are "living" or "controlled" radical polymerization processes. Such processes involve using a transfer agent that is specific for this purpose.

Generally, the preceding block copolymers can be obtained by any "living" or "controlled" polymerization process, such as, for example:

radical polymerization controlled by xanthates according to the teaching of Application WO 98/58974, radical polymerization controlled by dithioesters according to the teaching of Application WO 97/01478, polymerization using nitroxide precursors according to the teaching of Application WO 99/03894, radical polymerization controlled by dithiocarbamates according to the teaching of Application WO 99/31144, atom transfer radical polymerization (ATRP) according to the teaching of Application WO 96/30421, radical polymerization controlled by iniferters according to the teaching of Otu et al., Makromol. Chem. Rapid. Commun., 3, 127 (1982), radical polymerization controlled by degenerative transfer of iodine according to the teaching of Tatemoto et al., Jap. 50, 127, 991 (1975), Daikin Kogyo Co Ltd Japan, and Matyjaszewski et al., Macromolecules, 28, 2093 (1995), group transfer polymerization according to the teaching of Webster O. W., "Group Transfer Polymerization", p. 580–588, in the "Encyclopedia of Polymer Science and Engineering", Vol. 7, edited by H. F. Mark, N. M. Bikales, C. G. Overberger and G. Menges, Wiley Interscience, New York, 1987, radical polymerization controlled by tetraphenylethane derivatives (D. Braun et al., Macromol. Symp., 111, 63 (1996)), radical polymerization controlled by organocobalt complexes (Wayland et al., J. Am. Chem. Soc., 116, 7973 (1994)).

Preferred transfer agents for implementing a controlled polymerization process are agents comprising a dithioester group, a thioether-thione group, a dithiocarbamate group, or a xanthate group.

A Preferred polymerization process is a living radical polymerization using xanthates.

A "living" or "controlled" radical polymerization process used to make block copolymers comprises for example the steps of:

a) reacting an ethylenically unsaturated, preferably mono-α-ethylenically unsaturated, hydrophobic or hydrophilic monomer, at least a free radicals source compound, and a transfer agent, to obtain a first block, the transfer agent being linked to said first block, b1) reacting the first block, an ethylenically unsaturated, preferably mono-α-ethylenically unsaturated, hydrophobic or hydrophilic monomer, and, optionally, at least a radical source compound, to obtain a di-block copolymer, b2) optionally, repeating n times (n being equal to or greater than 0) step b1) to obtain a (n-2)-block copolymer, and then c) optionally, reacting the transfer agent with means to render it inactive, or to remove it.

For example, a "living" or "controlled" radical polymerization process used to make the di-block copolymers comprises the steps of:

a) reacting an ethylenically unsaturated, preferably mono-α-ethylenically unsaturated, hydrophobic or hydrophilic monomer, at least a free radicals source compound, and a transfer agent, to obtain a first block, the transfer agent being bounded to said first block, b) reacting the first block, an ethylenically unsaturated, preferably mono-α-ethylenically unsaturated, hydrophobic or hydrophilic monomer, and, optionally, at least a radical source compound, to obtain a di-block copolymer, and then c) optionally, reacting the transfer agent with means to render it inactive, or to remove it.

During step a), a first block of the polymer is synthesized with a hydrophilic or hydrophobic nature, according to the nature and the amount of the monomers used. During step b), b1), or b2), another block of the polymer is synthesized.

Examples of transfer agents are transfer agents of formula (I):

(I)

wherein:

R represents an $R^2O-$, $R^2R^{'2}N-$ or $R^3-$ group, $R^2$ and $R^{'2}$, which are identical or different, representing (i) an alkyl, acyl, aryl, alkene or alkyne group or (ii) an optionally aromatic, saturated or unsaturated carbonaceous ring or (iii) a saturated or unsaturated heterocycle, it being possible for these groups and rings (i), (ii) and (iii) to be substituted, $R^3$ representing H, Cl, an alkyl, aryl, alkene or alkyne group, an optionally substituted, saturated or unsaturated (hetero)cycle, an alkylthio, alkoxycarbonyl, aryloxycarbonyl, carboxyl, acyloxy, carbamoyl, cyano, dialkyl- or diarylphosphonato, or dialkyl- or diarylphosphinato group, or a polymer chain, R1 represents (i) an optionally substituted alkyl, acyl, aryl, alkene or alkyne group or (ii) a carbonaceous ring which is saturated or unsaturated and which is optionally subsituted or aromatic or (iii) an optionally substituted, saturated or unsaturated heterocycle or a polymer chain, and The R1, $R^2$, $R^{'2}$ and $R^3$ groups can be substituted by substituted phenyl or alkyl groups, substituted aromatic groups or the following groups: oxo, alkoxycarbonyl or aryloxycarbonyl (—COOR), carboxyl (—COOH), acyloxy (—O$_2$CR), carbamoyl (—CONR$_2$), cyano (—CN), alkylcarbonyl, alkylarylcarbonyl, arylcarbonyl, arylalkylcarbonyl, isocyanato, phthalimido, maleimido, succinimido, amidino, guanidino, hydroxyl (—OH), amino (—NR$_2$), halogen, allyl, epoxy, alkoxy (—OR), S-alkyl, S-aryl or silyl, groups exhibiting a hydrophilic or ionic nature, such as alkaline salts of carboxylic acids or alkaline salts of sulphonic acid, poly(alkylene oxide) (PEO, PPO) chains, or cationic substituents (quaternary ammonium salts), R representing an alkyl or aryl group.

Preferably, the transfer agent of formula (I) is a dithiocarbonate chosen from the compounds of following formulae (IA), (IB) and (IC):

(IA)

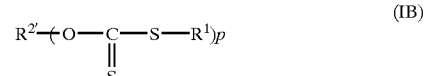

(IB)

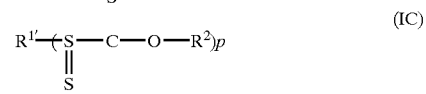

(IC)

wherein:

$R^2$ and $R^{2'}$ represent (i) an alkyl, acyl, aryl, alkene or alkyne group or (ii) an optionally aromatic, saturated or unsaturated carbonaceous ring or (iii) a saturated or unsaturated heterocycle, it being possible for these groups and rings (i), (ii) and (iii) to be substituted, $R^1$ and $R^{1'}$ represent (i) an optionally substituted alkyl, acyl, aryl, alkene or alkyne group or (ii) a carbonaceous ring which is saturated or unsaturated and which is optionally substituted or aromatic or (iii) an optionally substituted, saturated or unsaturated heterocycle or a polymer chain, and p is between 2 and 10.

According to the above described process, if all the successive polymerizations are carried out in the same reactor, it is generally preferable for all the monomers used during one stage to have been consumed before the polymerization of the following stage begins, therefore before the new monomers are introduced. However, it may happen that the hydrophobic or hydrophilic monomers of the preceding stage are still present in the reactor during the polymerization of the following block. In this case, these monomers generally do not represent more than 5 mol % of all the monomers and they participate in the following polymerization by contributing to the introduction of the hydrophobic or hydrophilic units into the following block.

The block copolymers prepared according to this polymerization process can be simply di-blocks, with a hydrophobic block and a hydrophilic block, or even triblocks, with either a hydrophilic block framed by two hydrophobic blocks or a hydrophobic block framed by two hydrophilic blocks.

The polymerization can be carried out in an aqueous and/or organic solvent medium, such as tetrahydrofuran or a linear, cyclic or branched $C_1$–$C_8$ aliphatic alcohol, such as methanol, ethanol or cyclohexanol, or a diol, such as ethylene glycol. An alcoholic solvent is more particularly recommended in the case where the hydrophilic monomers are acrylic acid (AA), acrylamide (AM), 2-acrylamido-2-methylpropanesulphonic acid (AMPS) and styrenesulphonate (SS) and the hydrophobic monomers are n-butyl acrylate, isobutyl acrylate, 2-ethylhexyl acrylate or t-butyl acrylate. The polymerization can also be also be carried out in a neat form, or according to a latex type process.

In a preferred embodiment, the hydrophobic block is a polybutylacrylate block, and the hydrophilic block is a polyacrylic acid block. In this embodiment, the ratio between the weight-average molecular weight of the hydrophilic block and the weight-average molecular weight of the hydrophobic block is preferably from 1 to 5. In this embodiment, the weight-average molecular weight of the hydrophobic block is comprised between 1000 g/mol and 10000 g/mol, and the weight-average molecular weight of the hydrophilic block is preferably comprised between 1000 g/mol and 50000 g/mol.

A process to obtain the aqueous suspension of nanoparticles comprises the step of mixing water, the organic the water-insoluble agrochemical active ingredient dissolved in a water-miscible solvent, and the amphiphilic compound. The amphiphilic compound may be added to water or to the solution comprising the organic water-insoluble agrochemical active ingredient, prior to mixing them. Mixing may be performed by any means, such as a conventional mixing device. When mixing water and the organic water-insoluble agrochemical active ingredient, said water-insoluble organic agrochemical active ingredient precipitates to form solid nanoparticles, usually in a crystal form.

It is believed that the amphiphilic compound has an effect at the interface of the active ingredient and water, which allows to obtain particles with the desired size and/or with a desired stability.

The above described process is particularly simple and economical. It avoids performing milling, emulsification (using a homogenizer), atomizing steps, or other high-energy steps.

In a preferred embodiment, a premix comprising a solvent of a water-insoluble organic agrochemical active ingredient, the active ingredient and the amphiphilic compound, dissolved in the solvent is prepared, and then mixed with water. Dissolution may be eased by heating. Mixing with water is for example carried out by pouring the premix into water.

In another embodiment, a premix comprising a solvent of a water-insoluble-organic active ingredient, and the active ingredient, dissolved in the solvent is prepared, and then mixed with a premix of water and the amphiphilic compound.

Usually, the amphiphilic compound is comprised in a mixture wherein it is soluble, either a water-based mixture, or a mixture comprising an organic water-insoluble agrochemical ingredient.

As the water is added, the amphiphilic compound (at least the hydrophobic moiety thereof) and the organic water-insoluble agrochemical active ingredient precipitate to form nanoparticles comprising the organic water-insoluble agrochemical active ingredient. Said nanoparticles are in suspension in water.

The mixing ratio between the solvent, or premix, and water is preferably comprised between 0.5 and 2.

In a particular embodiment, the obtained suspension of nanoparticles is re-diluted in water. This dilution improves the stability of the suspension. It may also lead to the concentration suitable for the use of the organic agrochemical active ingredient.

In a further embodiment, the solvent may be removed, for example by distillation.

Aqueous suspensions may be used as such. They may be for example applied on a field, by spraying.

In a particular embodiment of the invention, the water comprised in the aqueous suspension is removed, for example by freeze-drying or evaporating, to obtain dry solid nanoparticles. Said dry solid nanoparticles may be in an agglomerate form. The dried solid nanoparticles, in an agglomerate form or not, are then rehydrated with water to obtain an aqueous suspension of the nanoparticles. Drying the suspension may allow easier handling and cost-effective transportation.

Some illustrative but non-limiting examples are provided hereunder for the better understanding of the invention.

EXAMPLES

Amphiphilic Compound A

Amphiphilic compound A is alpha-{2,4,6-tris[1-(phenyl) ethyl]phenyl}-omega-hydroxy poly(oxyethelene)-poly (oxypropylene) copolymer comprising from 2 to 8 moles of poly(oxypropylene) units and 16–30 units of poly (oxyeythylene) units, Soprophor 796/P, marketed by Rhodia Amphiphilic Compound B Amphiphilic compound B is a di-block polybutylacrylate-polyacrylic acid (pBA-b-pAA) copolymer comprising a xanthate end-chain. The weight-average molecular weight of the pBA block is 3000 g/mol, the weight-average molecular weight of the pAA block is 12000 g/mol.

This block copolymer is prepared by using a living polymerization process with a Xanthate transfer agent.

Example 1

0.5 weight % of Amphiphilic compound B, 1 weight % of atrazine and methanol are mixed in a first beaker, to obtain 60 g of a solvent solution. 40 g of distilled water is poured into a second beaker. The two beakers are placed on separate heating plates with magnetic stirrers to ensure moderate agitation during heating. The solution and the water are heated to 35° C. Temperature is monitored with temperature probes. Atrazine and Amphiphilic compound B are perfectly soluble at this temperature. The solvent solution is then poured into the water and the resultant mixture. A suspension of nanopaticles in water is obtained. It is then further diluted ten times (1:10).

A particle size analysis is made, using a Malvern Mastersizer S version 2.18 device, and a size analysis performed assuming a polydisperse model and the Standard-Wet (3OHD) presentation that assumes the particle is suspended in water. The mass median diameter of the nanoparticles is 520 nm, 90% of the particles having a diameter of lower than 6.17 μm. More than 75% of the particles have a diameter of lower than 1060 nm.

Example 2

The procedure of example 1 is carried out, using 0.1 weight % of Amphiphilic compound B, and 0.1 weight % of atrazine, dissolved in 19.45 g of methanol, and using 30 g water. The mass median diameter is 350 nm, 90% of the particles having a diameter lower than 1.53 μm. More than 75% of the particles have a diameter of lower than 1060 nm.

Example 3

In a first beaker 0.5 g of atrazine (1 weight %) is dissolved in 24.5 g of methanol, at 35° C. In a second beaker 0.5 g of Amphiphilic Compound A (1 weight %) is dissolved in 24.5 g of distilled water. The two beakers are placed on separate heating plates with magnetic stirrers to ensure moderate agitation during heating. The solution and the water are heated to 35° C. Temperature is monitored with temperature probes. The solvent solution is then poured into the water and the resultant mixture. A suspension of nanoparticles in water is obtained. It is then further diluted ten times (1:10).

The mass median diameter of the nanoparticles is 300 nm, 90% of the particles having a diameter lower than 6.37 μm. More than 75% of the particles have a diameter of lower than 1060 nm.

What is claimed is:

1. An aqueous suspension of nanoparticles, said nanoparticles having a solid core comprising:
   an amphiphilic compound comprising at least one hydrophilic moiety and at least one hydrophobic moiety, and
   at least 50 parts by weight of an organic water-insoluble agrochemical active ingredient for 100 parts of the amphiphilic compound,
   wherein more than 50% of the nanoparticles have a diameter of lower than 1060 nm.

2. An aqueous suspension according to claim 1, wherein the hydrophilic moiety is a hydrophilic polymeric block.

3. An aqueous suspension according to claim 1, wherein the nanoparticles further comprise an organic solvent.

4. An aqueous suspension according to claim 1, wherein the nanoparticles comprise more than 100 parts by weight of the organic water-insoluble agrochemical active ingredient for 100 parts of the amphiphilic compound.

5. An aqueous suspension according to claim 1, wherein the nanoparticles comprise more than 500 parts by weight of the organic water-insoluble agrochemical active ingredient for 100 parts of the amphiphilic compound.

6. An aqueous suspension according to claim 1, wherein the organic water-insoluble agrochemical active ingredient is an insecticide, a nematicide, an herbicide, a fungicide, an aphicide, a miticide, or pesticide.

7. An aqueous suspension according to claim 6, wherein the organic water-insoluble agrochemical active ingredient is atrazine, cymoxanil, chlorothalanil, cyproconazole, and tebuconazole or a mixture thereof.

8. An aqueous suspension according to claim 1, wherein more than 50% of the nanoparticles have a diameter of lower than 600 nm.

9. An aqueous suspension according to claim 1, wherein the hydrophobic moiety is alpha-{2,4,6-tris[1-(phenyl)ethyl]phenyl}-omega-hydroxy group.

10. An aqueous suspension according to claim 9, wherein the hydrophilic polymer block is a poly(oxyethelene), poly(oxypropylene), or a poly(oxyethelene)-poly(oxypropylene) copolymer.

11. An aqueous suspension according to claim 2, wherein the hydrophobic moiety is a hydrophobic polymeric block.

12. An aqueous suspension according to claim 11, wherein:
   the amphiphilic compound has a number-average molecular weight comprised between 1000 and 50000 g/mol,
   the hydrophobic block(s) has a glass transition temperature lower than 30° C.

13. An aqueous composition according to claim 11, wherein the amphiphilic compound is a di-block copolymer comprising a hydrophilic block and a hydrophobic block.

14. An aqueous composition according to claim 13, wherein the di-block copolymer is obtained by a "living" polymerization process with the use of a transfer agent, comprising the steps of:
   a) reacting an ethylenically unsaturated hydrophobic or hydrophilic monomer, at least a free radicals source compound, and a transfer agent, to obtain a first block,
   b) reacting the first block, an ethylenically unsaturated hydrophobic or hydrophilic monomer, and, optionally, at least a radical source compound, to obtain a di-block copolymer, and then,
   c) optionally, reacting the transfer agent with means to render it inactive.

15. An aqueous suspension according to claim 14, wherein the transfer agent comprises a dithioester group, a thioester-thione group, a dithiocarbamate group, or a xanthate group.

16. An aqueous suspension according to claim 11, wherein the hydrophilic block comprises units deriving from monomers being:
   unsaturated ethylenic monocarboxylic acids, unsaturated ethylenic dicarboxylic acids,
   monoalkyl esters of unsaturated ethylenic dicarboxylic acids or N-substituted derivatives of monoalkyl esters of unsaturated ethylenic dicarboxylic,
   amides of unsaturated carboxylic acids,
   ethylenic monomers comprising a sulphonic acid group, their alkali metal or their ammonium salts.

17. An aqueous suspension according to claim 16, wherein the hydrophilic block comprises units deriving from monomers being acrylic acid (AA), methacrylic acid, itaconic acid, maleic acid, fumaric acid, 2-hydroxyethyl acrylate, 2-hydroxyethyl acrylate methacrylate, acrylamide (AM), methacrylamide, vinylsulphonic acid, vinylbenzenesulphonic acid, alpha-acrylamidomethylpropanesulphonic acid, 2-sulphoethyl methacrylate, 2-acrylamido-2-methylpropanesulphonic acid (AMPS), or styrenesulphonate (SS).

18. An aqueous suspension according to claim 11, wherein the hydrophobic block comprises units deriving from monomers being:

esters of acrylic acid and of methacrylic acid with hydrogenated or fluorinated $C_1$–$C_{12}$ alcohols, vinyl nitrites having from 3 to 12 carbon atoms, carboxylic acid vinyl esters, vinyl halides, vinylamine amides, unsaturated ethylenic monomers comprising a secondary, tertiary or quaternary amino group, unsaturated ethylenic monomers comprising a heterocyclic group comprising nitrogen, or styrene.

19. An aqueous suspension according to claim 18, wherein the hydrophobic block comprises units deriving from monomers being methyl acrylate, ethyl acrylate, propyl acrylate, n-butyl acrylate, isobutyl acrylate, 2-ethylhexyl acrylate, t-butyl acrylate, methyl methacrylate, ethyl methacrylate, n-butyl methacrylate, isobutyl methacrylate, acrylonitrile, methacrylonitrile, vinyl acetate, vinyl versatate, vinyl propionate vinylformamide, vinylacetamide, vinylpyridines, vinylimidazole, aminoalkyl (meth)acrylates, aminoalkyl(meth)acrylamides, dimethylaminoethyl acrylate, dimethylaminoethyl methacrylate, di-tert-butylaminoethyl acrylate, di-tert-butylaminoethyl methacrylate, dimethylaminomethylacrylamide or dimethylaminomethylacrylamide methacrylamide.

20. An aqueous suspension according to claim 11, wherein the hydrophobic block is a polybutylacrylate block, and the hydrophilic block is a polyacrylic acid block.

21. An aqueous suspension according to claim 20, wherein the ratio between the weight-average molecular weight of the hydrophilic block and the weight-average molecular weight of the hydrophobic block is from 1 to 5.

22. An aqueous suspension according to claim 21, wherein the weight-average molecular weight of the hydrophobic block is comprised between 1000 g/mol and 10000 g/mol, and the weight-average molecular weight of the hydrophilic block is comprised between 1000 g/mol and 50000 g/mol.

23. An aqueous suspension according to claim 1, obtained by a process comprising mixing water, the organic water-insoluble agrochemical active ingredient dissolved a water-miscible solvent, and the amphiphilic compound.

24. A process for protecting plants or for increasing crop yield, comprising the step of spreading an aqueous suspension according to claim 1.

* * * * *